(12) United States Patent
Creutz et al.

(10) Patent No.: US 7,683,119 B2
(45) Date of Patent: Mar. 23, 2010

(54) PROCESS FOR MAKING SILICONE EMULSIONS

(75) Inventors: Serge Creutz, Liege (BE); Dimitri Latour, Manage (BE); Henri Schirosi, Vitrival (BE); Karin Dubois, Manage (BE); Didier Vanderveken, Brussels (BE)

(73) Assignee: Dow Corning Corporation, Midland, MI (US)

( * ) Notice: Subject to any disclaimer, the term of this patent is extended or adjusted under 35 U.S.C. 154(b) by 691 days.

(21) Appl. No.: 11/464,140

(22) Filed: Aug. 11, 2006

(65) Prior Publication Data

US 2007/0043123 A1    Feb. 22, 2007

Related U.S. Application Data

(62) Division of application No. 10/432,095, filed on May 20, 2003, now Pat. No. 7,109,268.

(51) Int. Cl.
*C08L 83/04* (2006.01)
(52) U.S. Cl. .......................... 524/588; 516/53; 516/924
(58) Field of Classification Search ................. 524/588; 516/53, 924
See application file for complete search history.

(56) References Cited

U.S. PATENT DOCUMENTS

| 4,533,254 | A  | 8/1985  | Cook et al.     |
| 5,504,150 | A  | 4/1996  | Gilson et al.   |
| 5,563,189 | A  | 10/1996 | Hosokawa et al. |
| 5,741,850 | A  | 4/1998  | Hosokawa et al. |
| 5,806,975 | A  | 9/1998  | Hosokawa et al. |
| 6,232,396 | B1 | 5/2001  | Dong et al.     |
| 6,252,100 | B1 | 6/2001  | Herzig          |

FOREIGN PATENT DOCUMENTS

| EP | 0245658 A3    | 11/1987 |
| EP | 0771629 A1    | 5/1997  |
| EP | 0915122       | 5/1999  |
| EP | 1013700 A2    | 6/2000  |
| EP | 0761724 B1    | 7/2000  |
| EP | 0874017 B1    | 8/2004  |
| EP | 1447423 B1    | 4/2006  |
| JP | 56109227      | 8/1981  |
| JP | 07-173294   * | 7/1995  |
| JP | 10052633      | 2/1998  |
| JP | 2000000449    | 1/2000  |
| WO | WO9704121     | 2/1997  |
| WO | WO9929762 A1  | 6/1999  |

OTHER PUBLICATIONS

English language abstract for JP56109227 extracted from espacenet.com database Feb. 15, 2007.
UK Search Report for GB0028666.6, date of search: May 15, 2001, on 1 page.
Communication of a notice of opposition for EP 1447423, European Patent Office, Jan. 26, 2007, 1 page.
Excerpts of Ullmann's Encyclopaedia of Industrial Chemistry (UEIC), "Continuous mixing of fluids", Jun. 15, 2000, 31 pages.
Excerpt of Ullmann's Encyclopaedia of Industrial Chemistry (UEIC), "Stirred-tank and Loop Reactors", Jun. 15, 2000, 15 pages.

* cited by examiner

*Primary Examiner*—Kuo-Liang Peng
(74) *Attorney, Agent, or Firm*—Howard & Howard Attorneys PLLC

(57) ABSTRACT

In a process for the production of a silicone in water emulsion in which a polysiloxane fluid, at least one surfactant and water are continuously fed to a high shear mixer in such proportions as to form a viscous oil in water emulsion which is continuously withdrawn from the mixer. The polysiloxane fluid may be a non-reactive fluid or may have reactive groups capable of taking part in a chain extension reaction. A desired emulsion particle size can be maintained by monitoring the pressure in the supply line at the inlet to the high shear mixer.

13 Claims, 1 Drawing Sheet

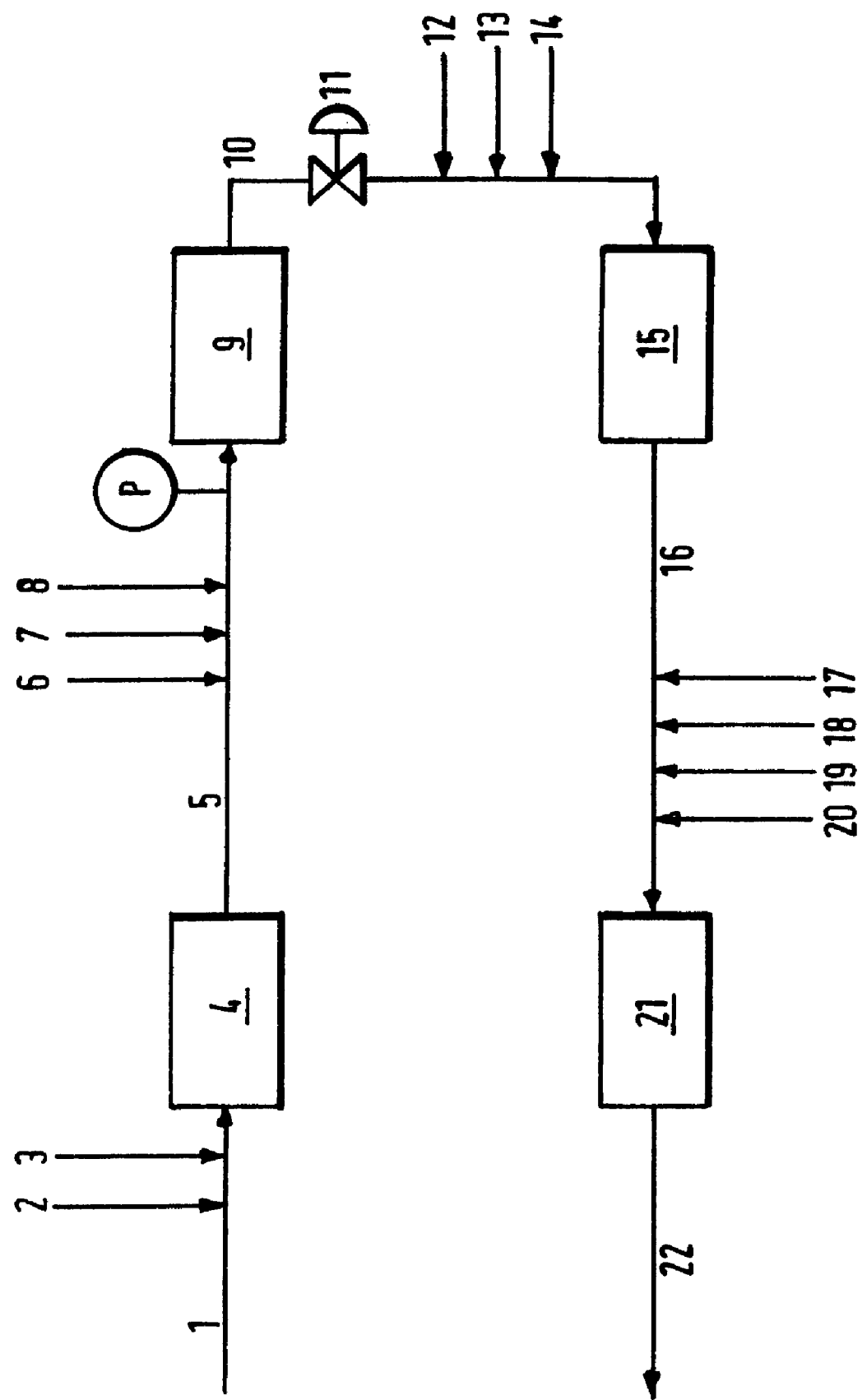

PROCESS FOR MAKING SILICONE EMULSIONS

CROSS-REFERENCE TO RELATED APPLICATIONS

This application is a divisional of Ser. No. 10/432,095, now U.S. Pat. No. 7,109,268, filed on May 20, 2003, which claims priority to and all the advantages of International Application No. PCT/EP01/13623, filed on Nov. 16, 2001, which claims priority to Great Britain Patent Application No. GB0114466.6, filed Jun. 14, 2001, and Great Britain Patent Application No. GB0028666.6, filed Nov. 24, 2000.

This invention relates to the production of silicone in water emulsions useful for example in toiletry and cosmetic products such as shampoos and skin creams, household cleaning products such as liquid detergents, textile process additives such as hydrophilic/hydrophobic modifiers and softeners, and release agents such as mould release and release coatings used for example on backings for adhesive products.

Silicone in water emulsions can be produced by emulsion polymerisation or by mechanical emulsification of a silicone polymer with one or more surfactants and water. Because silicones are highly hydrophobic, stable emulsions are difficult to produce mechanically and it is generally necessary to mix the silicone with a surfactant and a small amount of water under high mechanical shear to form a non-Newtonian "thick phase", which has a very high viscosity at low shear rates (much more viscous at low shear rate than the silicone polymer alone) and often exhibits a yield stress (viscoplastic behaviour). The resulting emulsion can be diluted with further water and surfactant. The highly viscous nature of this "thick phase" emulsion leads to a risk of uneven mixing or localised overheating when the process is carried out batchwise on an industrial scale.

U.S. Pat. No. 5,504,150 describes preparing emulsions by mixing organosilicon compounds, with a condensation catalyst and with a pressurized gas to cause foaming, feeding the foaming mixture down a reactor chamber, forming liquid polymers in the chamber by allowing the compounds to polymerise in the chamber. After polymerising the compounds, water and a surfactant are fed to the chamber and mixed with the foam in the chamber to form a water-in-oil emulsion containing the polymers. The emulsion is collected at the outlet of the reactor and inverted by shearing to an oil-in-water emulsion.

U.S. Pat. No. 5,806,975 describes a method of continuous emulsification of high viscosity organopolysiloxane gums in a compounding extruder. JP-A-12-449 describes the continuous production of an organopolysiloxane grease by feeding an organopolysiloxane with 0.1 to 100% emulsifier and 0.5 to 20% water to a rotary disc mixer.

EP-A-874017 describes a method of making a silicone in water emulsion comprising mixing materials comprising (I) a composition containing at least one polysiloxane, at least one organosilicon material that reacts with said polysiloxane by a chain extension reaction and a metal containing catalyst for said chain extension reaction, (II) at least one surfactant and (III) water to form a mixture; and emulsifying the mixture.

EP-A-915122 describes a process for preparing a silicone latex. The process comprises forming a premix of polydiorganosiloxane and crosslinker and then forming silicone latex by mixing surfactant and water with the premix. A process for the continuous preparation of the silicone latex using in-line dynamic mixers is also described.

BRIEF DESCRIPTION OF THE DRAWING

Other advantages of the present invention will be readily appreciated, as the same becomes better understood by reference to the following detailed description when considered in connection with the accompanying FIGURE, which is a diagrammatic flow chart of the process of the invention.

In a process according to a first aspect of the present invention for the production of a silicone in water emulsion, in which a polysiloxane fluid, at least one surfactant and water are continuously fed to a high shear mixer in such proportions as to form a viscous oil in water emulsion which is continuously withdrawn from the mixer, the polysiloxane, the surfactant and the water are fed into the high shear mixer through a single supply line and the pressure in the supply line at the inlet to the high shear mixer is monitored to be within 20% of a target pressure predetermined to give a desired emulsion particle size.

We believe that in the high shear mixer a crude water in oil premix is initially formed which is continuously transformed into the "thick phases" oil in water emulsion by the high shear conditions applied in the mixer.

We have found that in such a continuous process, the pressure at the inlet to the mixer correlates to the particle size of the emulsion eventually formed. The target pressure corresponding to a desired emulsion particle size is specific to each process/apparatus and composition, but can readily be determined by experiment. When the process is running continuously and the polysiloxane fluid, surfactant and water are being fed at a constant rate, the inlet pressure is a measure of the resistance to flow in the mixer. We have found that a variation of this inlet pressure by over 20% (in many cases a variation of over 10%) corresponds to a variation in the particle size of the emulsion product which is generally much greater than 20% and could even indicate that transformation into an oil in water emulsion is not taking place. The pressure in the supply line is preferably monitored continuously. If such a variation, particularly a drop in pressure, is observed or recorded, the process can be adjusted to restore the pressure level, for example by a slight increase in the proportion of surfactant fed to the mixer or by diverting the mixer outlet to scrap and stopping the continuous process. Automatic controls can be arranged to take such a step when a significant pressure variation occurs or a process operator can act when the pressure variation is noted.

The polysiloxane fluid can for example have a viscosity of at least 0.001, preferably at least 0.02 Pa·s up to 1000 Pa·s (1 or 20 up to 1000000 cps) or even up to 20000 Pa·s. The process of the invention is particularly suitable for continuous emulsification of substantially linear polydiorganosiloxanes such as polydimethylsiloxane although branched and/or cyclic polysiloxanes can also be emulsified. The polysiloxane fluid may be a non-reactive fluid, for example a linear polysiloxane tipped with trimethylsiloxy units, or may be a reactive fluid having reactive groups such as hydroxyl (either Si—OH or alcohol groups), amino, vinyl or Si—H groups. A reactive fluid may be reacted during or after the emulsification process as described in more detail below.

The surfactant can in general be any surfactant known for emulsification of silicones and can be a cationic, anionic, nonionic and/or amphoteric surfactant. Mixtures of surfactants of different types and/or different surfactants of the same type can be used. Combinations of ionic surfactants and nonionic surfactants may be particularly preferred. For many uses the surfactant needs to be chosen to give optimum compatibility with the product into which the silicone emulsion is to be incorporated.

Examples of non-ionic surfactants include polyoxyalkylene alkyl ethers such as polyethylene glycol long chain (9-22C, especially 12-14C) alkyl ether, polyoxyalkylene sorbitan ethers, polyoxyalkylene alkoxylate esters, polyoxyalkylene alkylphenol ethers, ethylene oxide propylene oxide copolymers, polyvinyl alcohol, glyceride esters and alkylpolysaccharides.

Examples of cationic surfactants include quaternary ammonium salts such as 8-22C alkyl trimethyl ammonium halides, particularly chlorides, 8-22C alkyl dimethyl benzyl ammonium halides or di(8-22C alkyl) dimethyl ammonium halides where the 8-22C alkyl group is for example octyl, decyl, dodecyl, hexadecyl, oleyl or octadecyl or tallow or coco alkyl groups, as well as corresponding salts of these materials, fatty amines and fatty acid amides and their derivatives, basic pyridinium compounds, quaternary ammonium bases of benzimidazolines and poly(ethoxylated/propoxylated) amines. Methosulphates, phosphates or acetates can be used as an alternative to halides.

Examples of suitable anionic surfactants include alkyl sulfates such as lauryl sulfate, polymers such as acrylates/$C_{10-30}$ alkyl acrylate crosspolymer, (6-20C alkyl) benzenesulfonic acids and salts, the sulfate esters of monoalkyl polyoxyethylene ethers, sulphonated glyceryl esters of fatty acids, salts of sulphonated monovalent alcohol esters, amides of amino sulphonic acids, sulphonated products of fatty acid nitriles, condensation products of naphthalene sulphonic acids with formaldehyde, alkali metal alkyl sulphates and ester sulphates, alkyl phosphates, sarcosinates and sulphonated olefins.

Examples of suitable amphoteric surfactants include cocamidopropyl betaine, cocamidopropyl hydroxysulphate, cocobetaine, sodium cocoamidoacetate, cocodimethyl betaine, N-coco-3-aminobutyric acid and imidazolinium carboxyl compounds.

Some anionic surfactants such as sulphonates and sulphates, for example alkyl benzene sulphonic acids, have some catalytic activity for condensation polymerisation of polysiloxanes, particularly silanol-functional polydiorganosiloxanes such as hydroxyl-terminated polydimethylsiloxanes, with themselves or in copolymerisation with organic or silane monomers and/or polymers having condensable functionality such as hydroxyl groups. The catalytic activity can be suppressed by a neutralising agent such as an organic amine, for example triethanolamine, or an inorganic base such as sodium hydroxide. It is usually preferred to avoid polymerisation before formation of the emulsion in the high shear mixer, because uncontrolled polymerisation may increase the viscosity of the polysiloxane so that it becomes too high to be properly emulsified when passing through the mixer. In addition, neutralization avoids corrosion and/or minimizes the need for special acid-resistant materials of construction for processing equipment. Subsequent acidification by addition of an acid or ion exchange, for example, treatment with an acidic ion exchange resin, will reactivate the catalytic properties of the sulphonate or sulphate surfactant if required.

Some cationic surfactants such as quaternary ammonium salts may also have catalytic activity for condensation polymerisation of polysiloxanes, particularly silanol-functional polydiorganosiloxanes such as hydroxyl-terminated polydimethylsiloxanes, with themselves or in copolymerisation with organic or silane monomers and/or polymers having condensable functionality such as hydroxyl groups. The catalytic activity may be activated by addition of an acid or base.

The surfactant can be added undiluted to the polysiloxane fluid or one or more surfactant can be premixed with water. Some surfactants are sold in aqueous form. The amount of surfactant added in the supply line to the high shear mixer is generally at least 0.2% by weight based on the polysiloxane fluid, preferably at least 0.5%, for example from 2% up to 10 or 20%. The amount of water present, including any water present in the surfactant composition, is generally at least 0.5% based on the polysiloxane fluid, preferably at least 1% up to 10 or 20% or even 30%. The polysiloxane content of the mixture fed into the high shear mixer is preferably from 70 to 99% by weight, most preferably 80 to 98%.

Where more than one surfactant is used, the surfactants can in general be premixed or can be added successively to the polysiloxane fluid. We have found that when an ionic (anionic or cationic) and a nonionic surfactant are used, an emulsion of lower and less variable particle size can be produced if the ionic surfactant is contacted with the polysiloxane fluid before it contacts the nonionic surfactant.

Thus according to another aspect of the invention a process for the production of a silicone in water emulsion, in which a polysiloxane fluid, at least one surfactant and water are continuously fed to a high shear mixer in such proportions as to form a viscous oil in water emulsion which is continuously withdrawn from the mixer, is characterised in that the polysiloxane fluid is contacted successively with an ionic surfactant and then with a non-ionic surfactant before being fed to the high shear mixer.

The polysiloxane fluid and the ionic surfactant are preferably mixed before contacting the non-ionic surfactant, for example they can be passed through a static mixer to achieve dispersion of the ionic surfactant throughout the polysiloxane before the non-ionic surfactant is added.

The "thick phase" oil in water emulsion which is continuously withdrawn from the high shear mixer usually needs to be diluted to reduce its viscosity before use. The "thick phase" can be diluted either continuously or batchwise. The amount of water added at this stage is generally at least 10% and preferably at least 20% based on the polysiloxane fluid, for example 30 to 150%. Further surfactant can be added at the dilution stage if desired, for example up to 10% by weight surfactant based on the polysiloxane fluid. The surfactant can be premixed with the water used for dilution or can be added separately. After addition of the water and optionally surfactant, the emulsion is thoroughly mixed, preferably in a high shear mixer, to ensure that it has been fully homogenised. If a more dilute emulsion than about 40% silicone is required, further water is preferably added in a subsequent dilution step which requires less vigorous mixing conditions.

The invention will now be described with reference to the single FIGURE of the accompanying drawings, which is a diagrammatic flow chart of the process of the invention.

Polysiloxane fluid is fed through main feeding line (1). A secondary feeding line (2) can be used for feeding a second polysiloxane, for example a polysiloxane which is reactive with the main polysiloxane fluid or forms a blend with it. A third feeding line (3) can be used for any other material to be blended with the polysiloxane, for example a catalyst for a reactive system. The polysiloxane and any materials fed through lines (2) and (3) are mixed in premixer (4), which is preferably a dynamic mixer but is for mixing purpose and has no special shear requirement. The secondary feed lines (2, 3) and mixer (4) can be omitted when producing emulsions from a single polysiloxane fluid.

The conduit (5) for polysiloxane fluid leaving mixer (4) forms a supply line leading towards high shear dynamic mixer (9). The supply line (5) is fed by first surfactant feeding line (6), second surfactant feeding line (7) and water feeding line (8). The order of injection of surfactants and water between lines (6, 7 and 8) can be changed depending on the formulation. Only one surfactant may be used, in which case one feed line (7) is not required. One of the surfactants may also already be diluted in water in which case it is possible that line (8) is not used. Main supply line (5) and those feed lines (6, 7 and/or 8) which are in use are all arranged to give continuous stable dosing of the material being fed, for example they preferably incorporate constant delivery pumps and may have back pressure valves between each pump and the main feed line (5). A mixer, for example a static mixer, may be included in supply line (5) between feeds (6 and 7) and/or between feeds (7 and 8). If a neutralising agent such as an amine is added to suppress the catalytic activity of an anionic surfactant, it can for example be added with that surfactant or added to the polysiloxane fluid, for example in feed line (2 or 3) before it contacts the surfactant.

The high shear dynamic mixer (9) used to emulsify the polysiloxane fluid, surfactant and water to a viscous oil in water emulsion can for example be an in-line, dynamic rotor/stator device such as those sold under the Trade Marks "TK Products Homomic Line Mill" or "Bematek" or "Greerco" or "Ross", often referred to as a colloid mill, or a rotary disc mixer of the type described in JP-A-2000-449, or a twin screw compounder of the type used for plastics extrusion. The mean residence time of the polysiloxane fluid mixture in the mixer (9), based on the total free volume in the body of the mixing device, is preferably between 0.1 and 600 seconds, particularly 1 to 60 seconds, and the degree of shear exerted by mixer (9) should be sufficient to emulsify the polysiloxane within this time. The residence time in the shear gap of an in-line rotor/stator mixer is preferably between 0.001 and 1 seconds, particularly 0.005 - 0.05 seconds. The circumferential speed of the mixer is preferably between 0.6 and 60 m/s, particularly 2-20 m/s. The emulsion produced in mixer (9) generally exhibits non-Newtonian fluid behaviour and has a substantially higher low shear viscosity than the polysiloxane fluid that it contains. The viscous emulsion is discharged from mixer (9) through thick phase transfer line (10).

A pressure sensor (P) is located in the supply line (5) at the inlet to mixer (9). The sensor (P) can be a pressure gauge of any type known in the chemicals industry for measuring pressure in continuously flowing liquids. For a given process system, emulsion composition, and total process flow rate, the pressure measured by (P) can be correlated with particle size of the emulsion produced and a target pressure determined. The pressure at (P) is preferably monitored continuously to check that it is within 20%, preferably within 10%, of the target pressure. We have found that maintaining the back pressure (P) within these limits is indicative of an emulsion of relatively uniform particle size so that 90% of the particles in the emulsion product have a size below 3M, usually below 2M, where M is the volume-based median size of the particles in the emulsion. The variation in particle size is much less than the variation found when using direct batch emulsification, for example by high pressure homogeniser. Routine testing of emulsion particle size can be reduced; in general, testing is only necessary if there has been a significant drop in back pressure (P).

The target pressure can be any pressure from 0.05 up to 20 or 40 bar or even higher, if the mechanical pressure constraints of the process allow. For forming an emulsion of particle size in the range 0.03 or 0.1 or 0.15 microns up to 20 microns, particularly a submicron particle size emulsion, from a nonreactive linear polysiloxane fluid, using apparatus such as that described in FIG. 1 and the conditions of Example 1, the target pressure is preferably in the range 2 to 20 bar, most preferably 4 to 6 bar.

A modular valve (11) is positioned in the thick phase transfer line (10). This valve (11) can be used to increase the pressure in line (10) and through mixer (9). It is not generally needed and is usually open when the process is running continuously in a steady state, but valve (11) is partially closed to increase pressure in line (10) and hence to control the back pressure (P) during start up when producing emulsions from a low viscosity polysiloxane, for example a fluid having a viscosity below 2 Pa·s.

A dilution water feeding line (12), an optional surfactant post-addition feed line (13) and an optional powder additive dosing line (14) all feed into the thick phase transfer line (10). In many cases the viscous oil in water emulsion is diluted with water alone, or the surfactant is incorporated in the water feed line (12), so that feed lines (13) and (14) may not be used. Surfactant used in dilution can be of any of the types described above. The thick phase, water and optional additives pass to a high shear dynamic mixer (15) in which the emulsion is diluted, for example to a silicone content of 60% by weight, and inverted to an oil in water emulsion. The mixer (15) can be of any of the types described above as suitable for mixer (9).

If an amine has been added before emulsification to suppress the catalytic activity of a sulphonate or sulphate surfactant, an acid can be added to the dilution water in feeding line (12) if it is desired to reactivate the catalytic properties of the sulphonate or sulphate surfactant. Alternatively an acid can be added, or the emulsion can be treated with an acidic ion exchange material, after dilution in the mixer (15).

The resulting oil in water emulsion is withdrawn from mixer (15) through transfer line (16). If a high silicone content emulsion, for example an emulsion of silicone content at least 40 or 50% by weight, is required, the line (16) can fed directly to the container in which the emulsion is to be sold or transported. If a more dilute emulsion is required, water can be added through final water addition line (17). Further feed lines (such as 18, 19, 20) for additives such as thickener, preservatives and/or antifoam can be used. Alternatively, further feed lines could be connected into transfer line (10) before the first dilution mixer (15) if the required formulation is of high silicone content. If water or additives have been added from any of feed lines (17 to 20) the emulsion passes through a dynamic mixer (21) used to ensure even dilution. The mixer (21) can be of a type as described above or may be of a more simple type, since mixing is its only purpose and high shear is not required. The emulsion issuing from mixer (21) through line (22), which has the silicone level required by a customer, passes to a container such as a drum, tote or road tanker.

In an alternative embodiment of the invention, the process can be worked in semi-continuous mode. In this embodiment, the feed lines (12 to 14 and 17 to 20) and mixers (15,21) can be omitted and the viscous oil in water emulsion in thick phase transfer line (10) downstream of valve (11) can be charged to an agitated dilution tank containing dilution water and any required additives. It may be possible for some formulations to feed the viscous emulsion produced in mixer (9) direct to containers in which it is shipped for dilution, for example by a customer whose products are in aqueous emulsion form.

In another alternative embodiment, the mixers (9 and 15) can be combined in a single apparatus such as a double disc refiner allowing injection of water between two mixing chambers. Alternatively the mixers (9, 15 and optionally 21) can be different barrels of a twin screw compounder allowing addition of water and other materials between barrels. A twin screw compounder may be the preferred mixer when handling polysiloxane fluids of very high viscosity, for example at least 1000 Pa·s., and is also suitable for emulsifying low viscosity fluids.

If the polysiloxane fluid contains reactive groups, it may undergo a chain extension reaction during the emulsification and dilution process. The materials to be emulsified can also comprise an organosiloxane material that reacts with the polysiloxane, preferably by a chain extension reaction. Such an organosiloxane material can for example be fed through line (2).

The invention thus includes a process for making a silicone in water emulsion comprising mixing a polysiloxane fluid having reactive groups capable of taking part in a chain extension reaction, a catalyst for said chain extension reaction, at least one surfactant and water and optionally an organosiloxane material that reacts with said polysiloxane by a chain extension reaction to form a mixture and emulsifying the mixture, characterized in that the polysiloxane fluid, at least one surfactant and water are continuously fed to a high shear mixer in such proportions as to form a viscous oil in water emulsion which is continuously withdrawn from the mixer, the catalyst and the organosiloxane material (if used) each being added either before or after the mixture is fed to the high shear mixer.

Examples of chain extension reactions are the hydrosilylation reaction in which a Si—H group reacts with an aliphatically unsaturated group in the presence of a platinum or rhodium containing catalyst, or the reaction of an Si—OH group with an alkoxy group present in an alkoxysilane, silicate or alkoxysiloxane, or a $CH_3COOSi-$, $R_2C=NOSi$ or SiH group in the presence of a metal containing catalyst, or the reaction of a Si—OH group with another Si—OH group in the presence of an acid catalyst, which can be an anionic surfactant as described above. The polysiloxane used in such reactions preferably comprises a substantially linear polymer, for example a polydiorganosiloxane, in which on average there is between one and two reactive groups per polymer and a majority, more preferably over 90%, and most preferably over 98% of the reactive groups are end-groups. The organosiloxane material that reacts with the polysiloxane by a chain extension reaction can be either a second polysiloxane or a material that acts as a chain extension agent. Preferably it is a linear polydiorganosiloxane in which at least a majority of its reactives are end-groups.

The catalyst in such a process can be added through line (3) and premixed with the polysiloxane in mixer (4), in which case a chain extension reaction may start in feed line (5) and mixer (9). The feed line (5) can be cooled, for example to about 0° C., to minimise such reaction. It may be preferred to add the catalyst to the emulsion after the emulsion has been formed in the high shear mixer (9). The catalyst can for example be incorporated in the water or aqueous surfactant added through line (12), which dilutes and inverts the emulsion, or with surfactant added through line (13), or can be added separately to the thick phase (10) through a feed such as (14). Addition through line (13) as a mixture with non-ionic surfactant has been found to be a particularly effective way of incorporating catalyst. Alternatively the catalyst can be incorporated in the surfactant feed (6 or 7) and/or the water feed (8) which contacts the organopolysiloxane feed (5) before the high shear mixer (9).

In a further alternative which is possible if the catalyst does not catalyse self-polymerisation of the polysiloxane, the catalyst can be added to the polysiloxane fluid through feed (3) or incorporated in feed (6, 7 or 8), with the organosiloxane material (chain extender) being added after the mixer (9). An example of such a catalyst is a metal-containing catalyst, particularly a platinum or rhodium containing catalyst, used with a vinyl terminated polydiorganosiloxane fluid and a Si—H terminated polydiorganosiloxane as the organosiloxane material co-reactant.

The invention is illustrated by the following Examples, in which parts and percentages are by weight.

EXAMPLES 1 AND 2

These Examples describe the preparation of an emulsion from a hydroxy-terminated polydimethylsiloxane fluid of viscosity 60 Pa·s. Both Examples prepared a thick oil in water emulsion continuously in a high shear dynamic mixer (9). In Example 1 the thick phase was diluted batchwise in a dilution tank. In Example 2 the thick phase was diluted continuously. The amounts of materials added through different lines are shown in Table 1 below.

TABLE 1

| Material | Weight % | Example 1 Reference in FIGURE | Weight % | Example 2 Reference in FIGURE |
|---|---|---|---|---|
| Polysiloxane fluid | 60 | 1 = 5 | 60 | 1 = 5 |
| Cocoalkyl pentaethoxy methyl ammonium methosulphate (pure cationic surfactant) | 1.9 | 6 | 1.9 | 6 |
| Coco trimethyl ammonium methosulfate (30% active aqueous cationic surfactant) | 1.93 | 7 | 1.93 | 7 |
| Coco trimethyl ammonium methosulfate (30% active) | 5.87 | Dilution tank | 5.87 | 13 |
| Demineralised water | 29.2 | dil tank | 21.6 | 12 |
| Demineralised water | | | 7.6 | 17 |
| Silicone antifoam | 0.1 | dil tank | 0.1 | 18 |
| Glycacil L (preservative) | 0.1 | dil tank | 0.1 | 19 |
| Phenoxyethanol (preservative) | 0.9 | dil tank | 0.9 | 20 |

The premix mixer (4) was not used. The high shear dynamic mixer (9) was a Homomic Line Mill running at 3800 rpm and a circumferential speed of 20 m/s with a rotor/stator with a gap of 0.5 mm. The pressure (P) at the high shear dynamic mixer inlet was maintained at about (within 10% of) 5 bars. During start-up an excess of the diluted surfactant feed (7) was used and the back pressure was increased as necessary by modular valve (11). When the feed rates were at the rates shown above the required pressure could be maintained with valve (11) open. The residence time of the polysiloxane in mixer (9), based on the total volume of the mixer body, was about 8 seconds.

In Example 1, the process was operated continuously for long enough to produce sufficient thick oil in water oil emulsion for one batch, then the continuous :part of the process was stopped. The dilution tank was agitated at 50 rpm and dilution was continued for 3 hours.

In Example 2, the high shear dilution mixer (15) was a Homomic Line Mill running at about 3500 rpm and a circumferential speed of 18 m/s with a gap of 0.5 mm. The second dilution mixer (21) was a Delmotte (Trade Mark) standard in-line dynamic mixer running at about 1500 rpm.

The non-volatile content of the emulsion produced was 65%. The volume-based median particle size D(v,0.5) was 0.38 microns in both Examples as measured by laser diffraction. The particle size of the emulsion produced in Example 1 was analysed and D(v,0.9) was 0.85 microns, i.e. 90% of the particles have particle size below 0.85 microns.

EXAMPLES 3 AND 4

Emulsions were produced by the process of EP874017 in which a chain extension reaction is carried out during emulsification. In both Examples the polysiloxane fluid comprised a vinyl-terminated linear polysiloxane of viscosity 10 Pa·s and a SiH-terminated short chain linear polysiloxane of viscosity 10 mPa·s. Both Examples prepared a thick oil in water emulsion continuously in a high shear dynamic mixer (9), although this emulsion was less viscous than the thick phase of Example 1. In Example 3 the thick phase was diluted batchwise. In Example 4 the thick phase was diluted continuously. The amounts of materials added through different lines are shown in Table 2 below.

TABLE 2

| Material | Example 3 Weight % | Reference in FIGURE | Example 4 Weight % | Reference in FIGURE |
|---|---|---|---|---|
| Vinyl polysiloxane | 65 | 1 | 65 | 1 |
| SiH polysiloxane | 2.04 | 2 | 2.04 | 2 |
| Hexadecyl trimethyl ammonium chloride (29% active aqueous cationic surfactant) | 7.8 | 6 | 7.8 | 6 |
| Demineralised water | 10 | 8 | 10 | 8 |
| Demineralised water | 14 | dilution tank | 14 | 12 |
| Platinum complex catalyst dispersed in non-ionic surfactant/water mixture | 0.031 of active Platinum | dil tank | 0.031 of active platinum | 13 |
| Cellulosize | 1 | dil tank | 1 | 14 |

The premix mixer (4) was a Delmotte mixer running at 1500 rpm. The high shear dynamic mixer 9 was a Homomic Line Mill running at 3000 rpm and a circumferential speed of 16 m/s with a rotor/stator gap of 0.5 mm. The pressure (P) at the high shear dynamic mixer inlet was 0.2 bars.

In Example 3, the continuous process was operated for a time to produce sufficient thick phase for one batch, then the continuous part of the process was stopped. The dilution tank was agitated at 50 rpm and dilution was continued for 1 hours. The median particle size of the oil in water emulsion produced was 10 microns and D(v,0.9) was measured as 20 microns.

In Example 4, the first high shear dilution mixer (15) was a Homomic Line Mill running at about 2000 rpm and a circumferential speed of 11 m/s with a rotor/stator gap of 0.5 mm. The second dilution mixer 21 was not used.

EXAMPLES 5 AND 6

Following the general procedure of Example 1, a thick phase silicone oil in water emulsion was produced from a trimethylsilyl-terminated polydimethylsiloxane fluid of viscosity 1 Pa·s by feeding the ingredients shown in Table 3 below. A static mixer was inserted in line (5) after surfactant feed (6) and before surfactant feed (7) so that the surfactant added at (6) was pre-dispersed in the polysiloxane fluid.

TABLE 3

| | % by weight | Example 5 Reference in FIGURE | % by weight | Example 6 Reference in FIGURE |
|---|---|---|---|---|
| Polysiloxane fluid | 86.0 | 1 | 86.0 | 1 |
| Sodium N-lauroyl sarcosinate 35% aqueous anionic surfactant | 6.5 | 6 | 6.5 | 7 |
| Tridecanol ethoxylate (7) 85% aqueous nonionic surfactant | 7.5 | 7 | 7.5 | 6 |

The thick phase was diluted in a dilution tank as described in Example 1. Particle size analysis of the emulsions produced gave the following results:

Example 5—Median particle size 212 nm, D(v0.9) 275 nm
Example 6—Median particle size 247 nm, D(v0.9) 400 nm.

As can be seen from the above results, stable emulsions were produced in both Examples 5 and 6, but a lower and more uniform particle size was produced in Example 5 where the polysiloxane was premixed with the anionic surfactant before addition of the nonionic surfactant.

EXAMPLES 7 TO 9

Silicone emulsions were produced using the general procedure and ingredients of Example 5, but in the relative proportions 87.7% polysiloxane fluid, 4.9% anionic surfactant and 7.4% aqueous nonionic surfactant. In Example 7 no mixer was used between surfactant feeds (6) and (7). In Example 8 there was medium mixing of the anionic surfactant and polysiloxane fluid (simple static mixer between feeds (6) and (7)). In Example 9 there was thorough mixing of the anionic surfactant and the polysiloxane fluid (dynamic mixer between feeds (6) and (7)). Stable emulsions were produced in all Examples. The mean particle sizes of the emulsions were:

Example 7—254 nm
Example 8—197 nm
Example 9—188 nm

EXAMPLE 10

A silicone emulsion was produced by a semi-continuous process of the type described in Example 1 from the materials listed in Table 4 below added at the points shown

TABLE 4

| | % by weight | Reference in FIGURE |
|---|---|---|
| Polysiloxane OH-terminated fluid | 91.7 | 1 |
| Triethanolamine | 4.6 | 3 |
| Sodium dodecyl benzene sulphonate anionic surfactant | 3.7 | 6 |
| Water | 8 | 8 |

Particle size analysis of the emulsion produced showed median particle size 173 nm and D(v0.9) 259 nm.

EXAMPLE 11

Following the process of Example 10, a silicone emulsion was produced by a semi-continuous process from the materials listed in Table 5 below added at the points shown

TABLE 5

| | % by weight | Reference in FIGURE |
|---|---|---|
| Polysiloxane OH-terminated fluid of viscosity 0.065 Pa·s | 89.4 | 1 |
| Triethanolamine | 3.39 | 3 |
| Dodecylbenzene sulphonic acid anionic surfactant | 4.74 | 6 |
| Water | 2.47 | 8 |

Particle size analysis of the emulsion produced showed:
Example 10—D(v,0.5) 173 nm and D(v,0.9) 259 nm.
Example 11—D(v,0.5) 196 nm and D(v,0.9) 272 nm.

EXAMPLES 12 AND 13

A silicone emulsion was produced by a semi-continuous process of the type described in Example 1 from the materials listed in Table 6 below added at the points shown. The Homomic Line Mill was operated at a rotor/stator gap of 0.35 mm, at a circumferential speed of 16 m/s.

TABLE 6

|  | % by weight (Ex. 12/Ex. 13) | Reference in FIGURE |
|---|---|---|
| Polysiloxane OH-terminated fluid of viscosity 0.065 Pa·s | 85.6/89.4 | 1 |
| Triethanolamine | 5.35/4.60 | 3 |
| Dodecylbenzene sulphonic acid surfactant | 7.47/4.70 | 6 |
| Water | 1.58/1.30 | 8 |

Particle size analysis of the resulting emulsions by dynamic light scattering showed particle size:
Example 12: D(v,0.5) 120 nm and D(v,0.9) 185 nm.
Example 13: D(v,0.5) 144 nm and D(v,0.9) 270 nm.

The invention claimed is:

1. A process for the production of a silicone in water emulsion in which a silanol-functional polydiorganosiloxane fluid, at least one surfactant and water are continuously fed to a high shear mixer in such proportions as to form a viscous oil in water emulsion which is continuously withdrawn from the mixer, characterised in that the silanol-functional polydiorganosiloxane fluid is contacted successively with an ionic surfactant and then with a non-ionic surfactant before being fed to the high shear mixer.

2. A process according to claim 1, characterised in that the silanol-functional polydiorganosiloxane fluid and ionic surfactant are mixed before being contacted with the non-ionic surfactant.

3. A process according to claim 1, characterised in that the silanol-functional polydiorganosiloxane content of the mixture fed into the high shear mixer is from 70 to 99% by weight.

4. A process according to claim 1, characterised in that the surfactants and water are fed separately to the silanol-functional polydiorganosiloxane fluid before being fed to the high shear mixer.

5. A process according to claim 1, characterised in that at least part of the water is added in the form of an aqueous surfactant solution to the silanol-functional polydiorganosiloxane fluid before being fed to the high shear mixer.

6. A process according to claim 1, characterised in that the viscosity of the silanol-functional polydiorganosiloxane fluid is in the range 0.001 to 1000 Pa·s.

7. A process according to claim 6, characterised in that the silanol-functional polydiorganosiloxane fluid is fed to the high shear mixer in a supply line, in that viscosity of the silanol-functional polydiorganosiloxane fluid is less than 2 Pa·s, and in that the pressure in the supply line is increased by a modular valve positioned downstream of the high shear mixer.

8. A process according to claim 1, characterised in that 90% of the particles in the emulsion product have a size below 3M, where M is the median size of the particles in the emulsion.

9. A process according to claim 1, characterised in that the silanol-functional polydiorganosiloxane and the surfactant is an anionic surfactant having catalytic activity for polymerisation of the silanol-functional polydiorganosiloxane.

10. A process according to claim 9, characterised in that an amine neutralising agent is contacted with the silanol-functional polydiorganosiloxane fluid and anionic surfactant to avoid polymerisation before formation of the emulsion in the high shear mixer.

11. A process according to claim 10, characterised in that the emulsion is acidified after emulsification to reactivate the catalytic properties of the anionic surfactant.

12. A process according to claim 1, characterised in that the silanol-functional polydiorganosiloxane and the surfactant is an anionic surfactant having catalytic activity for polymerization of the silanol-functional polydiorganosiloxane and in that a neutralising agent is contacted with the silanol-functional polydiorganosiloxane fluid and anionic surfactant to avoid polymerisation before formation of the emulsion in the high shear mixer.

13. A process according to claim 1, characterised in that the silanol-functional polydiorganosiloxane fluid also comprises an organosiloxane material that reacts with the silanol-functional polydiorganosiloxane fluid by a chain extension reaction, and in that a catalyst for the chain extension reaction is contacted with the silanol-functional polydiorganosiloxane fluid either before or after the high shear mixer.

* * * * *

UNITED STATES PATENT AND TRADEMARK OFFICE
CERTIFICATE OF CORRECTION

PATENT NO. : 7,683,119 B2
APPLICATION NO. : 11/464140
DATED : March 23, 2010
INVENTOR(S) : Serge Creutz et al.

It is certified that error appears in the above-identified patent and that said Letters Patent is hereby corrected as shown below:

On the title page, item [30], please include "Foreign Application Priority Data, November 24, 2000 (GB) GB0028666.6, June 14, 2001 (GB) GB0774466.6"

Please also add: "PCT Filed: November 16, 2001, PCT No. PCT/EP01/13623"

Signed and Sealed this

Sixth Day of July, 2010

David J. Kappos
*Director of the United States Patent and Trademark Office*